United States Patent
Tracy et al.

(10) Patent No.: US 11,950,618 B2
(45) Date of Patent: Apr. 9, 2024

(54) AQUEOUS FERMENTATION FEEDSTOCK AND A METHOD FOR THE PRODUCTION THEREOF

(71) Applicants: Superbrewed Food, Inc., New Castle, DE (US); AdvanceBio, LLC., Milford, OH (US)

(72) Inventors: Bryan P. Tracy, Wilmington, DE (US); Dale A. Monceaux, Loveland, OH (US)

(73) Assignees: SUPERBREWED FOOD INC., New Castle, DE (US); AdvanceBio, LLC, Milford, OH (US)

( * ) Notice: Subject to any disclaimer, the term of this patent is extended or adjusted under 35 U.S.C. 154(b) by 221 days.

(21) Appl. No.: 17/552,504

(22) Filed: Dec. 16, 2021

(65) Prior Publication Data

US 2022/0125079 A1 Apr. 28, 2022

Related U.S. Application Data

(63) Continuation of application No. 16/401,724, filed on May 2, 2019, now Pat. No. 11,229,226.

(60) Provisional application No. 62/667,544, filed on May 6, 2018.

(51) Int. Cl.
*C12P 7/14* (2006.01)
*A23L 7/104* (2016.01)
*C12N 9/26* (2006.01)

(52) U.S. Cl.
CPC ............ *A23L 7/104* (2016.08); *C12N 9/2414* (2013.01); *C12P 7/14* (2013.01); *C12Y 302/01001* (2013.01)

(58) Field of Classification Search
CPC .. C12N 9/2414; C12P 7/14; C12Y 302/01001
See application file for complete search history.

(56) References Cited

U.S. PATENT DOCUMENTS

2009/0142817 A1 6/2009 Norman et al.
2022/0243229 A1* 8/2022 Retsina .................... D21C 9/00

* cited by examiner

*Primary Examiner* — Tekchand Saidha
(74) *Attorney, Agent, or Firm* — Eva Leah Taksel

(57) ABSTRACT

Provided are dry-milling methods for producing an aqueous fermentation feedstock ingredient. The methods include providing a corn-processing filtration feed; filtering at least a fraction of said filtration feed on a microfiltration membrane, whereby an aqueous filtration permeate and a filtration retentate are formed; separating said filtration permeate from said filtration retentate, to form separated permeate and separated retentate; forming a fermentation feedstock comprising said separated permeate, and saccharifying and/or washing said separated retentate.

13 Claims, 1 Drawing Sheet

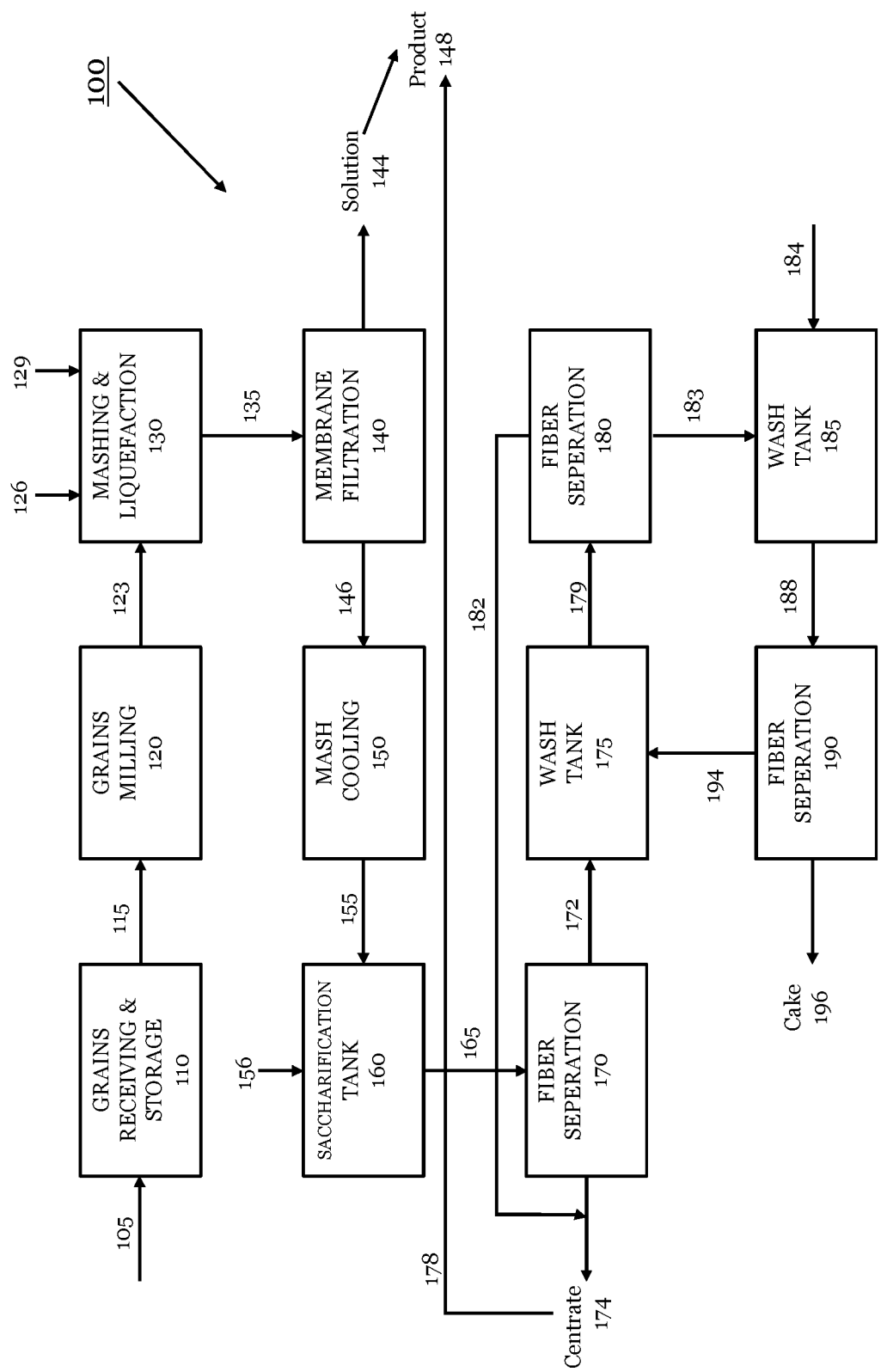

AQUEOUS FERMENTATION FEEDSTOCK AND A METHOD FOR THE PRODUCTION THEREOF

CROSS REFERENCE TO RELATED APPLICATIONS

This application is a continuation of U.S. Ser. No. 16/401,724, filed on May 2, 2019, which claims priority from U.S. provisional application 62/667,544, filed May 6, 2018.

BACKGROUND OF THE INVENTION

The cost of fermentation feedstock is a major contributor to the cost of fermentation products. There is, therefore, a strong need for low cost fermentation feedstock and for methods of producing thereof.

SUMMARY OF THE INVENTION

According to an embodiment, provided is a dry-milling method for producing an aqueous fermentation feedstock ingredient, comprising:
 (i) providing a corn-processing filtration feed comprising at least one water-soluble carbohydrate and water-insoluble matter;
 (ii) filtering at least a fraction of the filtration feed on a microfiltration membrane; whereby an aqueous filtration permeate, comprising the water-soluble carbohydrates, and a filtration retentate comprising the water-insoluble matter, are formed;
 (iii) separating the filtration permeate from the filtration retentate, to form separated permeate and separated retentate;
 (iv) forming a fermentation feedstock comprising the separated permeate, and;
 (v) treating the separated retentate, wherein the treating comprises saccharifying and/or washing.

According to an embodiment, provided is a method for producing the aqueous fermentation feedstock, wherein the providing a corn-processing filtration feed comprises providing corn kernels, comminuting the provided corn kernels, whereby comminuted corn kernels are formed, forming an aqueous slurry comprising the comminuted corn kernels, and treating the aqueous slurry with an enzyme composition comprising alpha-amylase enzymes, whereby a liquefied corn mash is formed.

According to an embodiment, provided is a method for producing the liquefied corn mash, wherein the providing a corn-processing filtration feed further comprises treating the liquefied corn mash with an enzyme composition comprising gluco-amylase enzymes, whereby a saccharified corn mash is formed.

According to an embodiment, provided is a method for producing the aqueous fermentation feedstock, further comprising a first washing the retentate with a first aqueous washing solution, wherein the first aqueous washing solution optionally comprises glucose and/or gluco-amylase, whereby a first washed retentate and a first wash solution are formed, and separating the first washed retentate from the first wash solution, whereby separated first washed retentate and separated first wash solution are formed, wherein the separated first wash solution comprises glucose and optionally gluco-amylase.

According to an embodiment, provided is a method for producing the aqueous fermentation feedstock, comprising treating the separated first wash solution with an enzyme composition comprising gluco-amylase enzymes, whereby saccharified first wash solution is formed.

According to an embodiment, provided is a method for producing the aqueous fermentation feedstock, wherein the providing a corn-processing filtration feed comprises blending at least a fraction of the separated first wash solution with liquefied corn mash, whereby a liquefied blend is formed, and treating the liquefied blend with an enzyme composition comprising gluco-amylase enzymes, whereby a saccharified corn mash is formed.

According to an embodiment, provided is a method for producing the aqueous fermentation feedstock, further comprising a second washing the separated first washed retentate with a second aqueous washing solution, whereby a second washed retentate and a second wash solution are formed and separating the second washed retentate from the second wash solution, whereby separated second washed retentate and separate second wash solution are formed, wherein the separated second wash solution comprises glucose and optionally gluco-amylase. According to an embodiment, the second wash solution comprises at least a fraction of the first aqueous washing solution.

According to an embodiment, provided is a method for producing the liquefied corn mash, further comprising a first washing the retentate with a first aqueous washing solution, wherein the first aqueous washing solution optionally comprises glucose and/or gluco-amylase, whereby a first washed retentate and a first wash solution are formed, and separating the first washed retentate from the first wash solution, whereby separated first washed retentate and separated first wash solution are formed, wherein the separated first wash solution comprises glucose and optionally gluco-amylase.

According to an embodiment, provided is a method for producing the liquefied corn mash, comprising treating the separated first wash solution with an enzyme composition comprising gluco-amylase enzymes, whereby saccharified first wash solution is formed.

According to an embodiment, provided is a method for producing the liquefied corn mash, wherein the providing a corn-processing filtration feed comprises blending at least a fraction of the separated first wash solution with liquefied corn mash, whereby a liquefied blend is formed, and treating the liquefied blend with an enzyme composition comprising gluco-amylase enzymes, whereby a saccharified corn mash is formed.

According to an embodiment, provided is a method for producing the liquefied corn mash, further comprising a second washing the separated first washed retentate with a second aqueous washing solution, whereby a second washed retentate and a second wash solution are formed and separating the second washed retentate from the second wash solution, whereby separated second washed retentate and separate second wash solution are formed, wherein the separated second wash solution comprises glucose and optionally gluco-amylase.

According to an embodiment, provided is a method for producing the liquefied corn mash, wherein the second wash solution comprises at least a fraction of the first aqueous washing solution.

According to an embodiment, provided is a method for producing the aqueous fermentation feedstock, wherein the separated retentate is treated with an enzyme composition comprising gluco-amylase enzymes, whereby saccharified retentate is formed.

According to an embodiment, provided is a method for producing the aqueous fermentation feedstock, wherein the saccharified retentate is treated and wherein the treating comprises at least one of separation of water-insoluble matter, first washing or first washing followed by second washing, whereby at least one aqueous solution comprising water-soluble carbohydrate is formed.

According to an embodiment, provided is a method for producing the aqueous fermentation feedstock, comprising combining at least a fraction of the separated retentate with at least a fraction of the liquefied corn mash to form a liquefied corn mash blend and treating the liquefied corn mash blend with an enzyme composition comprising glucoamylase enzymes, whereby saccharified corn mash blend is formed.

According to an embodiment, provided is a method for producing the aqueous fermentation feedstock, wherein the separated permeate comprises:
(i) glucose at a concentration in the range between 50 gram/Liter and 280 gram/Liter;
(ii) optionally dextrose oligomers at a concentration in the range between 50 gram/Liter and 280 gram/Liter;
(iii) optionally slurried particles of less than 0.5 micron;
(iv) optionally slurried particles of more than 0.5 micron at a concentration of less than 10 gram/Liter;
(v) optionally ash at a concentration in the range between 2 gram/Liter and 10 gram/Liter;
(vi) optionally lactate at a concentration in the range between 1 gram/Liter and 10 gram/Liter;
(vii) optionally protein at a concentration in the range between 10 gram/Liter and 40 gram/Liter;
(viii) optionally corn oil at a concentration of less than 5 gram/Liter; and/or (ix) optionally glycerol at a concentration in the range between 2 gram/Liter and 15 gram/Liter.

According to an embodiment, provided is a method for producing the aqueous fermentation feedstock, wherein the separated permeate is characterized by being sterile.

According to an embodiment, provided is a method for producing the aqueous fermentation feedstock, wherein the duration of the treating with alpha-amylase enzymes is in the range between 30 minutes and 300 minutes.

According to an embodiment, provided is a method for producing the aqueous fermentation feedstock, wherein the treating further comprises grinding of the slurry.

According to an embodiment, provided is a method for producing the aqueous fermentation feedstock, wherein the treating further comprises jet-cooking of the slurry.

According to an embodiment, provided is a method for producing the aqueous fermentation feedstock, wherein the microfiltration membrane is selected from the group consisting of sintered stainless-steel membranes, polymeric membranes and ceramic membranes.

According to an embodiment, provided is a method for producing the aqueous fermentation feedstock, wherein the microfiltration membrane is sintered stainless-steel membrane with ceramic coating.

According to an embodiment, provided is a method for producing the aqueous fermentation feedstock, wherein the ceramic coating comprises titanium oxide.

According to an embodiment, provided is a method for producing the aqueous fermentation feedstock, wherein the microfiltration membrane is characterized by porosity in the range between 0.01 micron and 0.5 micron.

According to an embodiment, provided is a method for producing the aqueous fermentation feedstock, wherein the filtering is characterized by at least one of:
(i) feed, permeate and retentate temperature ranging between 100 and 210 degrees Fahrenheit;
(ii) feed pressure ranging between 2 and 10 atmospheres gauge;
(iii) retentate pressure ranging between 2 and 10 atmospheres gauge;
(iv) permeate pressure ranging between 1 and 8 atmospheres gauge
(v) circulation or feed flow rate that creates a linear velocity within the membranes of at least 15 feet per second; and
(vi) transmembrane pressure drop ranging between 1 and 10 atmospheres gauge.

According to an embodiment, provided is a method for the production of single-cell protein, comprising culturing selected organisms in the aqueous fermentation feedstock.

BRIEF DESCRIPTION OF THE DRAWING

The accompanying drawing, which is incorporated in and constitute part of this specification, illustrate some embodiments of this invention and, with the detailed description of the embodiments given below, serves to explain the principles of the invention.

FIG. 1 is a flow diagram showing a method for producing the aqueous fermentation feedstock, in accordance with exemplary embodiment of present invention.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description, which follows, and in part will be obvious from the description, or may be learned by practice of the invention. It is to be understood that both the foregoing general description and the following detailed description are exemplary and explanatory only and are not restrictive of the invention, as claimed.

As used herein SCP refers to Single-Cell Protein.

Unless indicated otherwise, percent is weight percent and ratio are weight/weight ratio.

According to an embodiment, provided is a dry-milling method for producing an aqueous fermentation feedstock ingredient, comprising:
(i) providing a corn-processing filtration feed comprising at least one water-soluble carbohydrate and water-insoluble matter;
(ii) filtering at least a fraction of the filtration feed on a microfiltration membrane; whereby an aqueous filtration permeate, comprising the water-soluble carbohydrates, and a filtration retentate comprising the water-insoluble matter, are formed;
(iii) separating the filtration permeate from the filtration retentate, to form separated permeate and separated retentate;
(iv) forming a fermentation feedstock comprising the separated permeate, and;
(v) treating the separated retentate, wherein the treating comprises saccharifying and/or washing.

According to an embodiment, provided is a method for producing the aqueous fermentation feedstock, wherein the providing a corn-processing filtration feed comprises providing corn kernels, comminuting the provided corn kernels, whereby comminuted corn kernels are formed, forming an aqueous slurry comprising the comminuted corn kernels. and treating the aqueous slurry with an enzyme composition comprising alpha-amylase enzymes, whereby a liquefied corn mash is formed.

According to an embodiment, provided is a method for producing the liquefied corn mash, wherein the providing a corn-processing filtration feed further comprises treating the liquefied corn mash with an enzyme composition comprising gluco-amylase enzymes, whereby a saccharified corn mash is formed.

According to an embodiment, provided is a method for producing the aqueous fermentation feedstock, further comprising a first washing the retentate with a first aqueous washing solution, wherein the first aqueous washing solution optionally comprises glucose and/or gluco-amylase, whereby a first washed retentate and a first wash solution are formed, and separating the first washed retentate from the first wash solution, whereby separated first washed retentate and separated first wash solution are formed, wherein the separated first wash solution comprises glucose and optionally gluco-amylase.

According to an embodiment, provided is a method for producing the aqueous fermentation feedstock, comprising treating the separated first wash solution with an enzyme composition comprising gluco-amylase enzymes, whereby saccharified first wash solution is formed.

According to an embodiment, provided is a method for producing the aqueous fermentation feedstock, wherein the providing a corn-processing filtration feed comprises blending at least a fraction of the separated first wash solution with liquefied corn mash, whereby a liquefied blend is formed, and treating the liquefied blend with an enzyme composition comprising gluco-amylase enzymes, whereby a saccharified corn mash is formed.

According to an embodiment, provided is a method for producing the aqueous fermentation feedstock, further comprising a second washing the separated first washed retentate with a second aqueous washing solution, whereby a second washed retentate and a second wash solution are formed and separating the second washed retentate from the second wash solution, whereby separated second washed retentate and separate second wash solution are formed, wherein the separated second wash solution comprises glucose and optionally gluco-amylase. According to an embodiment, the second wash solution comprises at least a fraction of the first aqueous washing solution.

According to an embodiment, provided is a method for producing the liquefied corn mash, further comprising a first washing the retentate with a first aqueous washing solution, wherein the first aqueous washing solution optionally comprises glucose and/or gluco-amylase, whereby a first washed retentate and a first wash solution are formed, and separating the first washed retentate from the first wash solution, whereby separated first washed retentate and separated first wash solution are formed, wherein the separated first wash solution comprises glucose and optionally gluco-amylase.

According to an embodiment, provided is a method for producing the liquefied corn mash, comprising treating the separated first wash solution with an enzyme composition comprising gluco-amylase enzymes, whereby saccharified first wash solution is formed.

According to an embodiment, provided is a method for producing the liquefied corn mash, wherein the providing a corn-processing filtration feed comprises blending at least a fraction of the separated first wash solution with liquefied corn mash, whereby a liquefied blend is formed, and treating the liquefied blend with an enzyme composition comprising gluco-amylase enzymes, whereby a saccharified corn mash is formed.

According to an embodiment, provided is a method for producing the liquefied corn mash, further comprising a second washing the separated first washed retentate with a second aqueous washing solution, whereby a second washed retentate and a second wash solution are formed and separating the second washed retentate from the second wash solution, whereby separated second washed retentate and separate second wash solution are formed, wherein the separated second wash solution comprises glucose and optionally gluco-amylase.

According to an embodiment, provided is a method for producing the liquefied corn mash, wherein the second wash solution comprises at least a fraction of the first aqueous washing solution.

According to an embodiment, provided is a method for producing the aqueous fermentation feedstock, wherein the separated retentate is treated with an enzyme composition comprising gluco-amylase enzymes, whereby saccharified retentate is formed.

According to an embodiment, provided is a method for producing the aqueous fermentation feedstock, wherein the saccharified retentate is treated and wherein the treating comprises at least one of separation of water-insoluble matter, first washing or first washing followed by second washing, whereby at least one aqueous solution comprising water-soluble carbohydrate is formed.

According to an embodiment, provided is a method for producing the aqueous fermentation feedstock, comprising combining at least a fraction of the separated retentate with at least a fraction of the liquefied corn mash to form a liquefied corn mash blend and treating the liquefied corn mash blend with an enzyme composition comprising gluco-amylase enzymes, whereby saccharified corn mash blend is formed.

According to an embodiment, provided is a method for producing the aqueous fermentation feedstock, wherein the separated permeate comprises:
(i) glucose at a concentration in the range between 50 gram/Liter and 280 gram/Liter, between 60 gram/Liter and 270 gram/Liter, between 70 gram/Liter and 260 gram/Liter;
(ii) optionally dextrose oligomers at a concentration in the range between 50 gram/Liter and 280 gram/Liter, range between 60 gram/Liter and 270 gram/Liter, range between 70 gram/Liter and 260 gram/Liter;
(iii) optionally slurried particles of less than 0.5 micron, less than 1.0 micron, less than 1.5 micron;
(iv) optionally slurried particles of more than 0.5 micron at a concentration of less than 10 gram/Liter, less than 15 gram/Liter, less than 20 gram/Liter;
(v) optionally ash at a concentration in the range between 2 gram/Liter and 10 gram/Liter, between 3 gram/Liter and 9 gram/Liter, between 4 gram/Liter and 8 gram/Liter;
(vi) optionally lactate at a concentration in the range between 1 gram/Liter and 10 gram/Liter, between 2 gram/Liter and 9 gram/Liter, between 3 gram/Liter and 8 gram/Liter;
(vii) optionally protein at a concentration in the range between 10 gram/Liter and 40 gram/Liter;
(viii) optionally corn oil at a concentration of less than 5 gram/Liter, of less than 7 gram/Liter, of less than 9 gram/Liter; and/or
(ix) optionally glycerol at a concentration in the range between 2 gram/Liter and 15 gram/Liter.

According to an embodiment, provided is a method for producing the aqueous fermentation feedstock, wherein the separated permeate is characterized by being sterile.

According to an embodiment, provided is a method for producing the aqueous fermentation feedstock, wherein the duration of the treating with alpha-amylase enzymes is in the range between 30 minutes and 300 minutes, between 40 minutes and 250 minutes, between 50 minutes and 200 minutes.

According to an embodiment, provided is a method for producing the aqueous fermentation feedstock, wherein the treating further comprises grinding of the slurry.

According to an embodiment, provided is a method for producing the aqueous fermentation feedstock, wherein the treating further comprises jet-cooking of the slurry.

According to an embodiment, provided is a method for producing the aqueous fermentation feedstock, wherein the microfiltration membrane is selected from the group consisting of sintered stainless-steel membranes, polymeric membranes and ceramic membranes.

According to an embodiment, provided is a method for producing the aqueous fermentation feedstock, wherein the microfiltration membrane is sintered stainless-steel membrane with ceramic coating.

According to an embodiment, provided is a method for producing the aqueous fermentation feedstock, wherein the ceramic coating comprises titanium oxide.

According to an embodiment, provided is a method for producing the aqueous fermentation feedstock, wherein the microfiltration membrane is characterized by porosity in the range between 0.01 micron and 0.5 micron.

According to an embodiment, provided is a method for producing the aqueous fermentation feedstock, wherein the filtering is characterized by at least one of:
(i) feed, permeate and retentate temperature ranging between 100 and 210 degrees Fahrenheit;
(ii) feed pressure ranging between 2 and 10 atmospheres gauge;
(iii) retentate pressure ranging between 2 and 10 atmospheres gauge;
(iv) permeate pressure ranging between 1 and 8 atmospheres gauge
(v) circulation or feed flow rate that creates a linear velocity within the membranes of at least 15 feet per second; and
(vi) transmembrane pressure drop ranging between 1 and 10 atmospheres gauge.

According to an embodiment, provided is a method for the production of single-cell protein, comprising culturing selected organisms in the aqueous fermentation feedstock.

FIG. 1 illustrates an exemplary method 100 for producing the aqueous fermentation feedstock, in accordance with some embodiment of present invention. Corn 105 is provided to the grains receiving and storage unit 110/In some embodiments, any type of grains, whole or fractionated that form a carbohydrate source can be provided as 105, that including but not limiting to: wheat, rice, ray, oats or the like. In some embodiments any type of biomass of a carbohydrate source can be provided as 105, that including but not limiting to: sugarcane, cassava, bagasse or the like. The provided corn grains 115 are milled at 120 and transferred as a corn meal 125 to mashing and liquefaction 130.

According to some embodiments, mashing and liquefaction 130 is conducted an enzymes composition 126 comprising alpha-amylase enzymes and with evaporator condensate 129. According to some embodiment of the mashing and liquefaction 130, the duration of said treating with alpha-amylase enzymes is in the range between 30 minutes and 300 minutes to produce liquefied mash 135. According to some embodiments the liquefied mash 135 temperature ranges from 160 to 200 degrees F.

According to exemplary method 100 the liquefied mash 135 is fed into the membrane filtration 140 unit to generate an aqueous filtration permeate solution 144 and a filtration retentate 146. According to some embodiments the membrane is selected from the group consisting of sintered stainless-steel membranes, polymeric membranes and ceramic membranes or sintered stainless-steel membrane with ceramic coating. According to some embodiments, the ceramic coating comprises titanium oxide. According to some embodiments the microfiltration membrane is characterized by porosity in the range between 0.01 micron and 0.5 micron. According to embodiments the filtration retentate 146 is subjected to mash cooling 150 to form a cooled filtration retentate 155. According to some embodiments the cooled filtration retentate 155 temperature ranges from 120 to 160 degrees F., and it is fed into the saccharification tank 160 with enzymes composition 156 comprising gluco-amylase enzymes to generate saccharified mash 165.

According to some embodiments the saccharified mash 165 is subjected to fiber separation 170 to form a separated glucose centrate 174 and fiber cake 172. According to some embodiments the separated glucose centrate 174 can comprises some gluco-amylase enzymes. According to some embodiments separated glucose centrate 174 is used as an aqueous fermentation feedstock. According to other embodiments, the permeate solution 144 is used as aqueous fermentation feedstock. According to some embodiments glucose centrate 174 is mixed 178 with the permeate solution 144 to form an aqueous fermentation feedstock 148.

According to some embodiments the fiber cake 172 is fed into the wash tank 175 to generate fiber slurry 179, According to some embodiments the wash solution comprises gluco-amylase enzymes, according to other embodiments the wash solution comprises glucose, according to other embodiments the wash solution comprises glucose and optionally gluco-amylase.

According to some embodiments, the fiber slurry 179 can be subjected to fiber separation 180 to form a separated glucose centrate 182 and fiber cake 183. According to some embodiments glucose centrate 182 is mixed with the glucose centrate 174. According to other embodiments glucose centrate 182 is used as a component of the wash solution used in wash tank 175.

According to some embodiments fiber cake 183 is fed into the wash tank 185 to generate fiber slurry 188, According to some embodiments the wash solution comprises an evaporator condensate 184. According to some embodiments the wash solution comprises gluco-amylase enzymes/According to other embodiments, the wash solution comprises glucose, according to other embodiments the wash solution comprises evaporator condensate 184, glucose and optionally gluco-amylase. According to some embodiments, the fiber slurry 188 can be subjected to fiber separation 190 to form a separated lean glucose centrate 194 and washed cake 196. According to some embodiments glucose lean centrate 194 is used as a component comprises wash solution used in wash tank 175.

The invention claimed is:

1. A method for the production of single-cell protein, comprising:
    (i) providing a corn-processing filtration feed comprising at least one water-soluble carbohydrate and water-insoluble matter;
    (ii) filtering at least a fraction of said filtration feed on a microfiltration membrane; whereby an aqueous filtration permeate, comprising said water-soluble carbohydrates, and a filtration retentate comprising said water-insoluble matter, are formed;
    (iii) separating said filtration permeate from said filtration retentate, to form separated permeate and separated retentate;
    (iv) forming a fermentation feedstock comprising said separated filtration permeate; and
    (v) culturing selected organisms in said fermentation feedstock.

2. The method of claim 1, wherein said providing a corn-processing filtration feed comprises providing corn kernels, comminuting said provided corn kernels, whereby comminuted corn kernels are formed, forming an aqueous slurry comprising said comminuted corn kernels, and treating said aqueous slurry with an enzyme composition comprising alpha-amylase enzymes, whereby a liquefied corn mash is formed.

3. The method of claim 2, wherein said providing a corn-processing filtration feed further comprises treating said liquefied corn mash with an enzyme composition comprising gluco-amylase enzymes, whereby a saccharified corn mash is formed.

4. The method of claim 1, wherein said separated permeate comprises:
    (i) glucose at a concentration in the range between 50 gram/Liter and 280 gram/Liter;
    (ii) optionally dextrose oligomers at a concentration in the range between 50 gram/Liter and 280 gram/Liter;
    (iii) optionally slurried particles of less than 0.5 micron;
    (iv) optionally slurried particles of more than 0.5 micron at a concentration of less than 10 gram/Liter;
    (v) optionally ash at a concentration in the range between 2 gram/Liter and 10 gram/Liter;
    (vi) optionally lactate at a concentration in the range between 1 gram/Liter and 10 gram/Liter;
    (vii) optionally protein at a concentration in the range between 10 gram/Liter and 40 gram/Liter;
    (viii) optionally corn oil at a concentration of less than 5 gram/Liter; and/or
    (ix) optionally glycerol at a concentration in the range between 2 gram/Liter and 15 gram/Liter.

5. The method of claim 1, wherein said separated permeate is characterized by being sterile.

6. The method of claim 2, wherein the duration of said treating with alpha-amylase enzymes is in the range between 30 minutes and 300 minutes.

7. The method of claim 2, wherein said treating further comprises grinding of said slurry.

8. The method of claim 2, wherein said treating further comprises jet-cooking of said slurry.

9. The method of claim 1, wherein said microfiltration membrane is selected from the group consisting of sintered stainless-steel membranes, polymeric membranes and ceramic membranes.

10. The method of claim 1, wherein said microfiltration membrane is sintered stainless-steel membrane with ceramic coating.

11. The method of claim 1, wherein said ceramic coating comprises titanium oxide.

12. The method of claim 1, wherein said microfiltration membrane is characterized by porosity in the range between 0.01 micron and 0.5 micron.

13. The method of claim 1, wherein said filtering is characterized by at least one of:
    (i) feed, permeate and retentate temperature ranging between 100 and 210 degrees Fahrenheit;
    (ii) feed pressure ranging between 2 and 10 atmospheres gauge;
    (iii) retentate pressure ranging between 2 and 10 atmospheres gauge;
    (iv) permeate pressure ranging between 1 and 8 atmospheres gauge
    (v) circulation or feed flow rate that creates a linear velocity within the membranes of at least 15 feet per second; and
    (vi) transmembrane pressure drop ranging between 1 and 10 atmospheres gauge.

* * * * *